(12) United States Patent
Plachetka et al.

(10) Patent No.: US 6,495,535 B1
(45) Date of Patent: Dec. 17, 2002

(54) HIGH POTENCY DIHYDROERGOTAMINE COMPOSITIONS

(75) Inventors: John R. Plachetka, Chapel Hill, NC (US); Donna Gilbert, Chapel Hill, NC (US)

(73) Assignee: Pozen Inc., Chapel Hill, NC (US)

( * ) Notice: Subject to any disclaimer, the term of this patent is extended or adjusted under 35 U.S.C. 154(b) by 0 days.

(21) Appl. No.: 09/526,474

(22) Filed: Mar. 15, 2000

Related U.S. Application Data

(60) Provisional application No. 60/126,333, filed on Mar. 26, 1999.

(51) Int. Cl.$^7$ .................. A61K 31/495; A61K 31/56
(52) U.S. Cl. ........................... 514/177; 514/250
(58) Field of Search ............................ 514/250, 177

(56) References Cited

U.S. PATENT DOCUMENTS 4,138,565 A  2/1979  Ehrhardt et al. ............ 544/346

FOREIGN PATENT DOCUMENTS

| BE | 881 967 | 6/1980 | |
| DE | 25 55 481 | 6/1977 | .......... A61K/31/48 |
| DE | 32 27 122 | 1/1984 | .......... A61K/31/48 |
| EP | 074 620 | 3/1983 | .......... A61K/47/00 |
| FR | 2 399 248 | 3/1979 | .......... A61K/31/48 |
| WO | WO 96/25190 | 8/1996 | .......... A61M/5/307 |

OTHER PUBLICATIONS

Physicians' Desk Reference 53 edition 1999; Dec. 1998 pp. 2059–2063.*
Drug Facts and Comparisons, 1985 p. 257c.*
Translation of AH1 above, BE 881 967.
Becker, et al., "Effectiveness of Subcutaneous Dihydroergotamine by Home Injection for Migraine," *Headache* 36(3):144–148 (1996).
Belgrade, et al., "Comparison of Single–Dose Meperidine, Butorphanol, and Dihydroergotamine in the Treatment of Vascular Headache," *Neurology* 39(4):590–592 (1989).
Klapper, et al., "Clinical Experience with Patient Administered Subcutaneous Dihydroergotamine Mesylate in Refractory Headaches," *Headache* 32(1):21–23 (1992).
Raskin, "Repetitive Intravenous Dihydroergotamine as Therapy for Intractable Migraine," *Neurology* 36(7):995–997 (1986).
Saadah, "Abortive Headache Therapy with Intramuscular Dihydroergotamine," *Headache* 32(1):18–20 (1992).
Schran, et al., "Bioequivalence and Safety of Subcutaneously and Intramuscularly Administered Dihydroergotamine in Healthy Volunteers," *Curr. Ther. Res.* 55(12):1501–1508 (1994).
Silberstein, et al., "Repetitive Intravenous DHE in the Treatment of Refractory Headache," *Headache* 30(6):334–339 (1990).
Welch, "Drug Therapy of Migraine," *New Eng. J. Med.* 329(20):1476–1483 (1993).
Winner, et al., "A Double–Blind Study of Subcutaneous Dihydroergotamine vs. Subcutaneous Sumatriptan in the Treatment of Acute Migraine," *Arch. Neurol.* 53:180–184 (1996).
Winner, et al., "Office–Based Treatment of Acute Migraine with Dihydroergotamine Mesylate," *Headache* 33(9):471–475 (1993).
Dialog abstract of AH1 above.
Dialog abstract of AI1 above.
Dialog abstract of AJ1 above.
Dialog abstract of AK1 above.
International Search Report for PCT/US00/06657.

* cited by examiner

*Primary Examiner*—Theodore J. Criares
*Assistant Examiner*—Jennifer Kim
(74) *Attorney, Agent, or Firm*—Michael A. Sanzo; Fitch, Even, Tabin & Flannery

(57) ABSTRACT

The present invention is directed to improved formulations for dihydroergotamine in which the drug is present at a concentration of at least 2.9 mM. The invention encompasses methods for using these formulations in treating patients for migraine headaches and the packaging of formulation into prefilled syringes for self-administration by patients.

18 Claims, 2 Drawing Sheets

HIGH POTENCY DIHYDROERGOTAMINE COMPOSITIONS

CROSS REFERENCE TO RELATED APPLICATIONS

The present application claims the benefit of U.S. Provisional application No. 60/126,333, filed on Mar. 26, 1999.

FIELD OF THE INVENTION

The present invention encompasses pharmaceutical compositions containing dihydroergotamine (DHE) and methods in which these pharmaceutical compositions are administered to patients, particularly for the treatment of migraine headaches. The invention also encompasses the packaging of injection syringes prefilled with DHE preparations.

BACKGROUND OF THE INVENTION

Dihydroergotamine (DHE) is an ergot alkaloid that was identified as an effective treatment for migraine nearly fifty years ago (Raskin, Neurology 36:995–997 (1986); Silberstein, et al., Headache 30:334–339 (1990); Saadah, Headache 32:18–20 (1992); and Winner, Headache 33:471–475 (1993)). It is presently marketed both as an injectable product (DHE 45®) and as a nasal spray (Migranal®). DHE is typically administered by intramuscular or intravenous injection (Belgrade, et al., Neurology 39:590–592 (1989); Winner, Headache 33:471–475 (1993)), but it is also effective when given subcutaneously (Klapper, et al. Headache 32:21–23 (1992); Winner, et al., Arch. Neurol. 53:180–184 (1996); and Becker, et al., Headache 36:144–148 (1996)).

Although effective in the treatment of migraine, DHE administration is often accompanied by side effects such as nausea, vomiting and chest pain (Winner, et al., Arch. Neurol. 53:180–184 (1996)). At least one side effect, nausea, occurs more frequently after intravenous administration than after intramuscular or intranasal administration. When given subcutaneously at a concentration of only 1.5 mM, DHE has been reported to cause nausea in nearly 16% of treated patients (Winner, et al., Arch. Neurol. 53: 80–184 (1996)). New drug formulations and methods for administering DHE which reduce its adverse side effects would represent a significant advance in migraine therapy.

SUMMARY OF THE INVENTION

The present invention is based upon the discovery that the side effect profile of DHE can be unexpectedly improved when the drug is administered to patients in a novel, high-potency form. More particularly, it has been found that when the concentration of DHE in compositions is increased from 1.5 mM (the concentration in commercially available injectable preparations) to 2.9 mM or more, side effects, particularly nausea, are reduced even though the total quantity of DHE administered remains constant.

In its first aspect, the invention is directed to a pharmaceutical composition in unit dose form containing DHE dissolved in a pharmaceutically acceptable liquid vehicle. The concentration of DHE must be at least 2.9 mM and a "unit dose" should contain a sufficient amount to be effective in the symptomatic treatment of migraine headache when administered to a patient. This means that enough drug must be given to significantly reduce or eliminate migraine-related pain. In order to preserve drug activity, steps should be taken to inhibit the oxidation of DHE. Preferably, this can be accomplished by dissolving sufficient $CO_2$ and/or $N_2$ compositions to retard oxidative degradation and/or including one or more antioxidants. Although any salt form of DHE can be effectively used in compositions, dihydroergotamine mesylate at a concentration of 2 mg/ml or more is preferred. A typical example of a formulation might contain 2 mg/ml of DHE in a vehicle containing glycerin and anhydrous alcohol in sterile water for injection, pH adjusted to 3.6 with methanesulfonic acids/sodium hydroxide. If desired, other agents may also be included in pharmaceutical preparations. For example, the rate at which DHE enters the bloodstream of a patient may be adjusted by including vasodilators or uptake enhancers (e.g., caffeine) in compositions.

The invention also includes a method of treating a patient for the symptoms associated with migraine headache by administering one or more unit doses of the pharmaceutical composition described above. Preferably, compositions will contain dihydroergotamine mesylate and sufficient dissolved $CO_2$ and/or $N_2$ to retard its oxidative degradation. Subcutaneous injection is preferred in order to obtain the greatest improvement in the side effect profile, but other routes of delivery may also be used. The total dosage of DHE that will be administered to a patient per migraine attack should generally be between 0.5 mg and 5.0 mg. The term "per migraine attack" refers to the period immediately preceding a migraine headache and extending for about the next twenty-four hours. Since headache may recur, it may be necessary to administer a second therapeutic dose of the drug during this period.

In addition, the invention is directed to a process for preparing a therapeutic package in which the unit dose pharmaceutical composition described above is made and then used to prefill a syringe for injection. As used herein, a "prefilled" syringe is one that has been loaded with pharmaceutical composition for a period of at least twenty-four hours prior to the time that it is administered to a patient. In a preferred embodiment, the prefilled syringes are enclosed in an opaque, sealed package from which oxygen has been excluded. For example, oxygen may be displaced with $CO_2$ and/or $N_2$. In addition to including these processes, the present invention also encompasses the therapeutic packages that are their end result.

A surprising discovery that has been made is that caffeine greatly increases the solubility of DHE in aqueous formulations. As a result, compositions having DHE at a concentration of greater than 4, 5 or 6 mM, can be obtained for administration to patients. Caffeine appears to be most effective when present in compositions roughly at a weight ratio of between 0.1:1 and 10:1 relative to DHE. In addition, there are some indications from animal studies that caffeine at high concentrations, e.g., at a 10:1 weight ratio relative to DHE improves drug absorption characteristics, e.g., by producing a more consistent time of absorption.

Based upon these findings, the invention is, in another aspect, directed to a pharmaceutical composition in unit dose form containing: a) DHE in an amount such that one or more unit doses are effective in the symptomatic treatment of migraine headache when administered to a patient; (b) a pharmaceutically acceptable liquid vehicle in which the DHE is dissolved at a concentration of at least 2.9 mM; and (c) caffeine at between a 0.1:1 and 10:1 weight ratio relative to DHE. The most preferred composition contains caffeine in a 1:1 weight ratio. In order to retard the rate of oxidative degradation of the composition, $CO_2$ and/or $N_2$ may be dissolved in preparations and one or more antioxidants may be added. Any salt of DHE may be used but the mesylate salt is generally preferred.

The compositions containing caffeine may be used in a method for the symptomatic treatment of patients suffering from migraine headache. Preferably, preparations are administered by subcutaneous injection and, in general, patients will receive a total dosage of between 0.5 and 5.0 mg per migraine attack. The compositions may also be used in a process for preparing a therapeutic package in which a unit dose is present in a prefilled injectable syringe. As part of the process, the prefilled syringes may be enclosed in an opaque, sealed package from which oxygen has been excluded. The invention includes not only these processes for making therapeutic packages but also the packages themselves.

Finally, the invention encompasses improved pharmaceutical compositions and treatment methods involving the combination of DHE at high concentration and caffeine. With respect to unit dose pharmaceutical compositions, the improvement comprises the presence of a concentration of DHE of at least 2 mg/ml; sufficient carbon dioxide and/or nitrogen to retard oxidative degradation; and caffeine at between a 0.1:1 and 10:1 weight ratio relative to DHE. The use of this composition results in an improved method for the symptomatic treatment of a patient suffering from or susceptible to the development of a migraine attack.

BRIEF DESCRIPTION OF THE FIGURES

FIG. 1 shows a flowchart for the manufacture of 6 liters of a DHE pharmaceutical composition. A unit dose of the formulation contains 2 mg of dihydroergotamine mesylate, USP, in 1.0 ml of glycerin, USP, ethyl alcohol, USP, and water for injection, USP, adjusted to a target pH of 3.6±0.2 with 0.1 M methanesulfonic acid and 0.1 M sodium hydroxide, NF (final concentration of DHE=2.9 mM). The bulk solution is sterile-filtered and then purged with sterile-filtered nitrogen. The solution may be dispensed either into disposable syringes or into 1.0 ml USP Type I ampules under aseptic filling conditions.

FIG. 2 shows the mean DHE plasma concentrations obtained in the experiments described in Example 2. Solid triangles=1 mg of Formula A-2 (2 mg/ml, 2.9 mM) sc; solid squares=1 mg Formula A-1 (1 mg/ml, 1.5 mM) sc; open squares=1 mg Formula E-2 (2 mg/ml) sc; open circles=1 mg Formula E-1 (1 mg/ml) sc; and solid diamonds=1 mg DHE 45® im.

FIG. 3 shows mean plasma DHE concentrations for the experiment described in Example 3. Open circles=1.0 mg DHE 45® im (1 mg/ml. 1.5 mM); darkened squares=1.2 mg MT 300 sc (2 mg/ml, 2.9 mM).

DETAILED DESCRIPTION OF THE INVENTION

Figure 1:
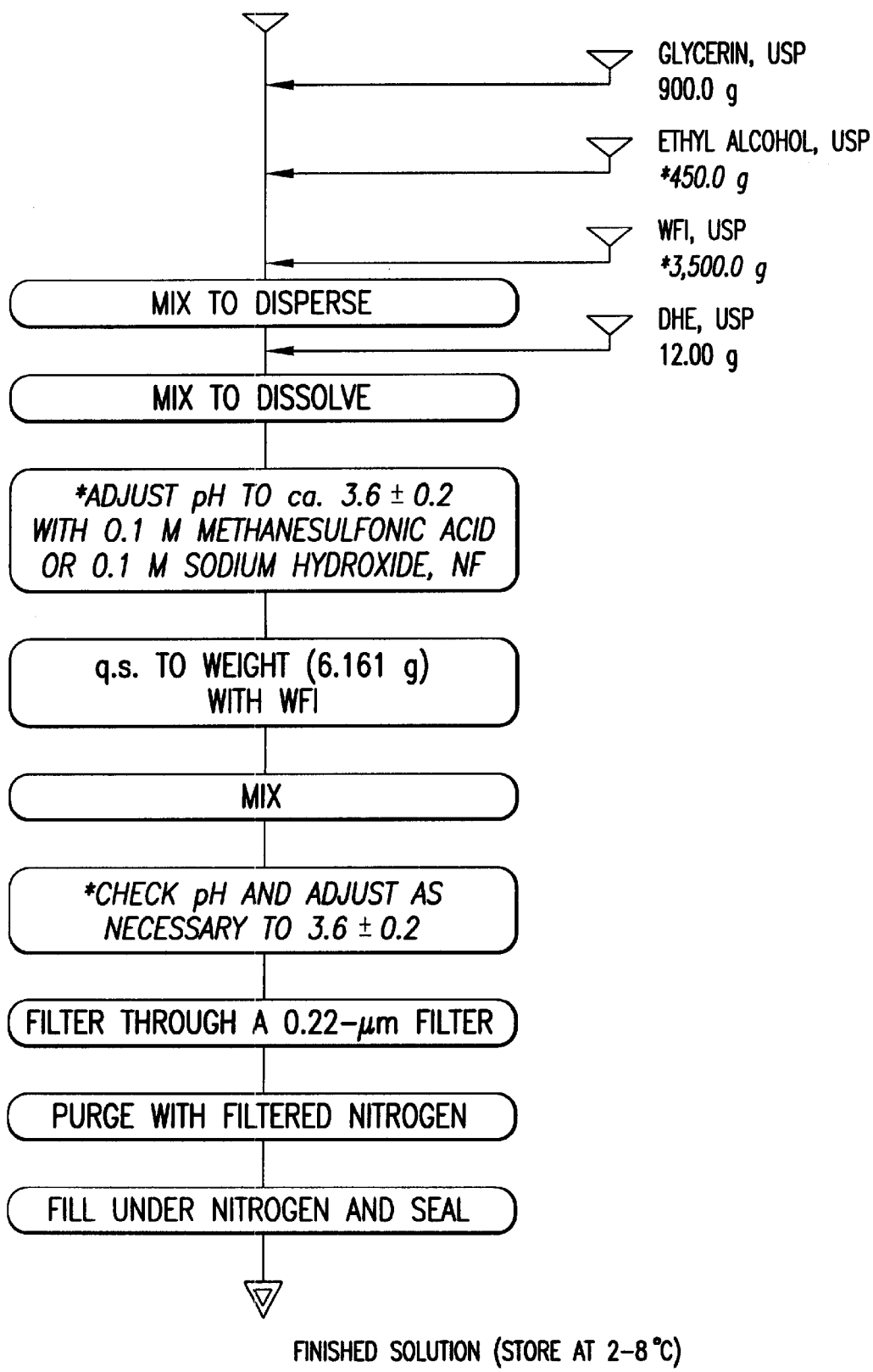
FIG. 1.

Migraine, as defined by the International Headache Society, affects at least 18 million women and 5.6 million men in the United States. Although DHE is known to be an effective treatment for migraine, its value is limited by a tendency to produce unacceptable side effects, particularly nausea. The present invention is based upon the discovery of a new formulation for DHE that, when administered to a migraine patient, maintains efficacy but reduces observed side effects. In addition to being directed to an improved drug formulation, the present invention also encompasses methods by which this formulation is used as well as packaging that should make the use of the formulation more convenient in clinical practice.

A. DHE Formulation

A formulation has been developed in which DHE is dissolved in a pharmaceutically acceptable liquid at a concentration of at least 2.9 mM. The DHE can be incorporated into formulations in any chemical form and administered to patients either as a free base or as a pharmaceutically acceptable salt. The most preferred formulation contains dihydroergotamine mesylate and caffeine at a 1:1 weight ratio.

Solutions can be prepared using water or physiologically compatible organic solvents such as ethanol, 1,2-propylene glycol, polyglycols, dimethyl sulfoxide, fatty alcohols, triglyercides, partial esters of glycerin and the like. Parenteral compositions are preferred and may include sterile isotonic saline, water, 1,3-butanediol, ethanol, 1,2-propylene glycol, polyglycols mixed with water, Ringer's solution, etc. In all cases, formulations may be prepared using methods that are standard in the art (see, e.g., *Remington's Pharmaceutical Sciences,* 16th ed., A. Oslo ed., Easton, Pa. (1980)). In order to prevent the oxidative degradation of DHE, preparations may be sparged with a non-oxidizing gas, e.g., nitrogen and/or $CO_2$. If desired, pharmaceutically acceptable antioxidants may also be incorporated into drug preparations. The components present in the most preferred DHE formulation are shown in Table 1 and a procedure for the large-scale preparation of a batch of formula is described in Example 1.

TABLE 1

DHE Formulation

| Ingredient[1] | Quantity per Unit Dose | Quantity per Batch of 6 Liters |
|---|---|---|
| Dihydroergotamine mesylate, USP | 2.0 mg | 12.00 g |
| Glycerin, USP | 150.0 mg | 900.0 g |
| Ethyl alcohol 100%, USP | 75.0 mg | 450.0 g |
| Sodium Hydroxide, NF | Negligible[2] | Negligible[2] |
| Methanesulfonic acid | Negligible[2] | Negligible[2] |
| Water for injection, USP | q.s. to 1.0 ml | q.s. to 6,161 g[3] |

[1] nitrogen and/or CO2 is used during sparging and filling operations
[2] 0.1 M methanesulfonic acid or 0.1 M sodium hydroxide, NF solutions are used to adjust the pH to 3.6 ± 0.2
[3] when formulated by weight, a density of 1.0268 is used to calculate the final weight of the bulk solution B. Treatment Method The total dosage of DHE administered to a patient should be at least the amount required to reduce or eliminate the pain associated with migraine headache. A single dose will usually be approximately 1 mg. This may be repeated if headache pain is not alleviated or if there is a recurrence of headache. Typically, the total dosage taken by a patient during a migraine episode will be between 0.5 mg and 5.0 mg. These dosages are simply guidelines and may be adjusted for an individual patient based upon clinical conditions and using methods well known in the art.

Although the number of patients experiencing adverse side effects is reduced with the present formulations compared to formulations containing a lower (1.5 mM) concentration of DHE, it is expected that they will still occur. Accordingly, the lowest dosage compatible with headache relief should generally be used. For example, a patient may initially attempt to alleviate pain by administering a dosage of 0.5 mg subcutaneously. If this proves to be insufficient, administration may be repeated. Once an effective dose has been established for a patient, it may be repeated in subsequent migraine attacks. It is generally expected that a dosage of about 1 mg should be sufficient to alleviate headache pain in most patients without producing undesirable side effects. Preparations should not be given in combination with vasoconstrictors, beta blockers, or macrolide antibiotics.

In the most preferred embodiment of this invention DHE is administered subcutaneously. However, alternative routes of administration in which drug is not immediately bioavailable but is instead progressively absorbed into a patient's bloodstream may also be used. Among these alternatives, intramuscular delivery is preferred and nasal, transdermal, intracutaneous, buccal, and sublingual routes may also be used. Specific dosage forms that may be used include aerosols, skin patches, parenterals and sustained release preparations. All dosage forms may be prepared using methods well known in the art (see, e.g., *Remington's Pharmaceutical Sciences*, 16th ed., A. Oslo ed., Easton, Pa. (1980)). DHE may be administered as either the sole active agent or in combination with other therapeutically active drugs.

C. Packaging

The DHE formulations described above can be packed in ampules or any other suitable container, but they are preferably provided in prefilled disposable syringes for self-administration by patients, with or without an autoinjector. Typically, each syringe will contain a single dose of DHE. For example, a syringe may contain 1.0 ml of a 2 mg/ml formulation prepared as described above. In order to prevent the oxidative destruction of drug, syringes should be filled under an inert gas such as nitrogen and/or $CO_2$. It is also preferred that the syringes be enclosed within a sealed package from which oxygen has been excluded. This may be accomplished by vacuum-packing syringes or by displacing oxygen with nitrogen and/or $CO_2$. When an inert gas is used to displace oxygen, packages should be relatively impermeable to diffusion after sealing. Also, the packages should preferably be opaque to ordinary light. Standard methods for filling and packaging syringes are well known in the art and may be used in conjunction with the present invention.

EXAMPLES

Example 1
Manufacture of Formulation

FIG. 1 is a flowchart for the manufacture of 6 liters (approximately 6,000 ampules or prefilled syringes). In order to carry out the depicted process, the following steps should be followed:

(a) Depyrogenate glass ampules to be used in the filling process.

(b) Add 900.0 g of glycerin, USP, to a suitable container.

(c) Add 450.0 g of ethyl alcohol 100%, USP, to the container.

(d) Add about 3,500 g of water for injection, USP, to the container.

(e) Mix until dispersed. Sparge with filtered nitrogen, NF, while mixing.

(f) While protecting the container from light, charge 12.00 grams of dihydroergotamine mesylate, USP, to the glycerin, ethyl alcohol, and water, and mix until dissolved. Continue to sparge with filtered nitrogen, NF, while mixing.

(g) Determine the pH of the solution and adjust with 0.1 M methanesulfonic acid or 0.1 M sodium hydroxide, as required, to obtain a pH value of 3.6±0.2.

(h) Add a requisite quantity of water to q.s. to 6,161 g and mix while continuing to sparge with filtered nitrogen, NF.

(i) Determine the pH of the solution and adjust as necessary with 0.1 M methanesulfonic acid or 0.1 M sodium hydroxide to obtain a pH value of 3.6±0.2.

(j) Sterile-filter the bulk solution through a sterile 0.22 μm filter. At the end of filtration, perform bubble point testing (specification: 45 psi).

(k) Purge the filtered bulk solution with filtered nitrogen, NF.

(l) Flush the headspace of the bulk solution with filtered nitrogen, NF, throughout the filling process.

(m) Fill each sterile 1 ml ampule with 1.13 g±0.02 g solution.

(n) Flame-seal each ampule.

(o) Protect from light.

Example 2
Efficacy, Tolerance, and Pharmacokinetics of DHE Formulations

The objectives of the experiments discussed in this example are to compare the local tolerability and absorption kinetics of experimental preparations of DHE (designated as "MT 300") and a commercially available preparation, DHE 45®. Aqueous and ethanol/glycerin/water formulations of DHE are tested at concentrations of 1 mg/ml (1.5 mM) and 2 mg/ml (2.9 mM). The trial is designed as a randomized, open label, 3-period incomplete crossover study of the four different MT 300 treatments, DHE 45®, and placebo. In the initial protocol, individual doses of DHE are always 1 mg regardless of the formulation or product. MT 300 and placebo are administered subcutaneously into the upper arm and DHE 45® was administered intramuscularly into the deltoid muscle. Safety evaluations included assessment of clinically adverse events throughout the study period and clinical laboratory assessments following each dose. Subjects are also evaluated for any local irritant effects of the various formulations.

Eighteen subjects participate in this study and 16 subjects complete the study. Subjects are divided into three groups and each subject received three treatments. The duration of each treatment period is a single day followed by a washout period of the same length. Serial blood samples for pharmacokinetic analysis are collected for 6 hours after each dose. At least two of the treatments administered to each subject are MT 300. The dosing regimens for the three groups are summarized in Table 2.

TABLE 2

| Dosing Regimen | | |
|---|---|---|
| Group 1 (n = 6) | Group 2 (n = 7*) | Group 3 (n = 5) |
| Formulation A-1: Aqueous DHE, 1 mg/ml sc | Formulation A-2: Aqueous DHE, 2 mg/ml sc | Formulation E-2: Ethanol/glycerin/water DHE, 2 mg/ml sc |
| Aqueous placebo, sc | Formulation A-1: Aqueous DHE, 1 mg/ml sc | DHE 45 ® im |
| Formulation E-1: Ethanol/glycerin/water DHE, 1 mg/ml sc | Formulation E-2: Ethanol/glycerin/water DHE, 2 mg/ml sc | Formulation A-2: Aqueous DHE, 2 mg/ml sc |

*One subject drops out of the study after the first dose and one subject drops out after the second dose.

Results—Exposure

A total of 18 subjects enter this 3-period crossover trial. Because of the limited sample size and crossover design, all formulations of MT 300 are combined for the purpose of describing exposure and tolerance. As shown in Table 3, the 18 subjects treated in this trial actually receive 40 doses of MT 300, 5 doses of DHE 45®, and 6 doses of placebo.

TABLE 3

Treatment Exposure

|  | MT 300 | DHE 45 ® | Placebo |
|---|---|---|---|
| Total subjects exposed to single doses | 18 | 5 | 6 |
| Total number of single doses administered | 40 | 5 | 6 |

Results—Tolerance

There are no serious adverse events in this study. Two subjects withdraw from the study early due to difficulty with blood sampling required for pharmacokinetic sampling. Mild pain at the injection site occurs in a single subject following administration of the MT 300 formulation, and in two of five patients on DHE 45°. None of the subjects experience more than mild pain.

The higher incidence of pain with DHE 45® may be related to the intramuscular route of administration. The injection site reactions are of little clinical significance. The adverse events experienced are predominantly mild in severity and, overall, the doses of MT 300 may be better tolerated than DHE 45°.

Results—Pharmacokinetics

Figure 2:
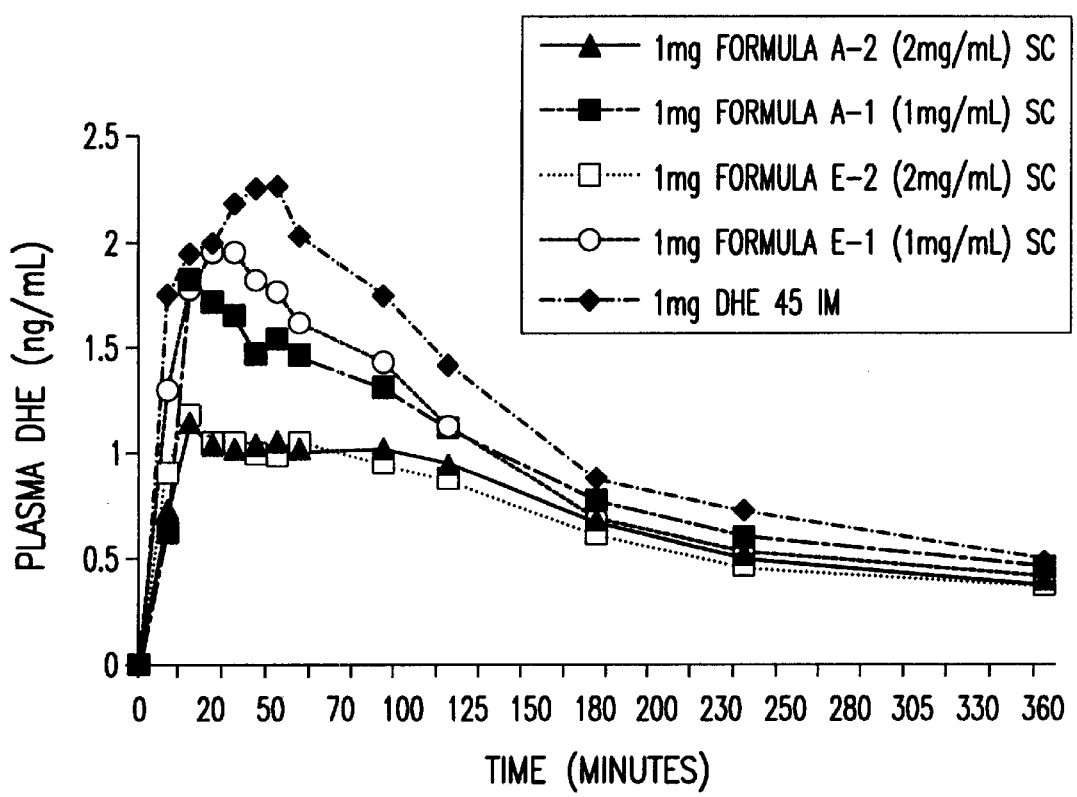
FIG. 2.

The mean plasma DHE concentration-time profiles following subcutaneous administration of the 1 mg/ml (1.5 mM), formulations of MT 300 (both aqueous and ethanol/glycerin/water vehicles) shows somewhat lower peak plasma levels compared to an intramuscular injection of 1 mg DHE (see FIG. 2). These results indicate that the absorption of sc DHE is somewhat less rapid than after im DHE 45°.

In contrast, the mean peak DHE concentrations following subcutaneous administration of both 2 mg/ml (2.9 mM) formulations of MT 300 are approximately 40% to 50% lower than those following either the 1 mg/ml (1.5 mM) formulation of MT 300 or im DHE 45®. Thus, the vehicles do not appear to influence the absorption of DHE while the concentration of DHE in the formulations appear to have an effect. This difference in rate of absorption following the subcutaneous administration of the MT 300, 2 mg/ml formulations may be the result of a local venoconstrictive action of a high concentration of DHE and/or the smaller surface area for DHE diffusion associated with the smaller volume administered (0.5 ml vs 1 ml).

Example 3
Direct Comparison of Tolerance and Pharmacokinetics

The study described above in Example 2 utilizes an incomplete crossover design. This protocol is amended to provide a direct comparison of the tolerance and pharmacokinetics of a 2 mg/ml (2.9 mM) formulation of MT 300 (Formulation A-2) and DHE 45®. The present experiment is a randomized, open-label, two period, parallel group, crossover study comparing subcutaneous administration of 1.2 mg of MT 300 and intramuscular administration of 1 mg of DHE 45°. Plasma dihydroergotamine and the 8-hydroxydihydroergotamine metabolite are measured with an LC/MS/MS method, with a LLOQ of 50 pg/ml for both DHE and 8-OH DHE. Serial blood samples are collected for 72 hours after the dose. Seven of 8 subjects complete this study. One subject withdraws from the study due to difficulty in obtaining the blood samples. The adverse event profile is similar to that observed in the study of Example 2.

Figure 3:
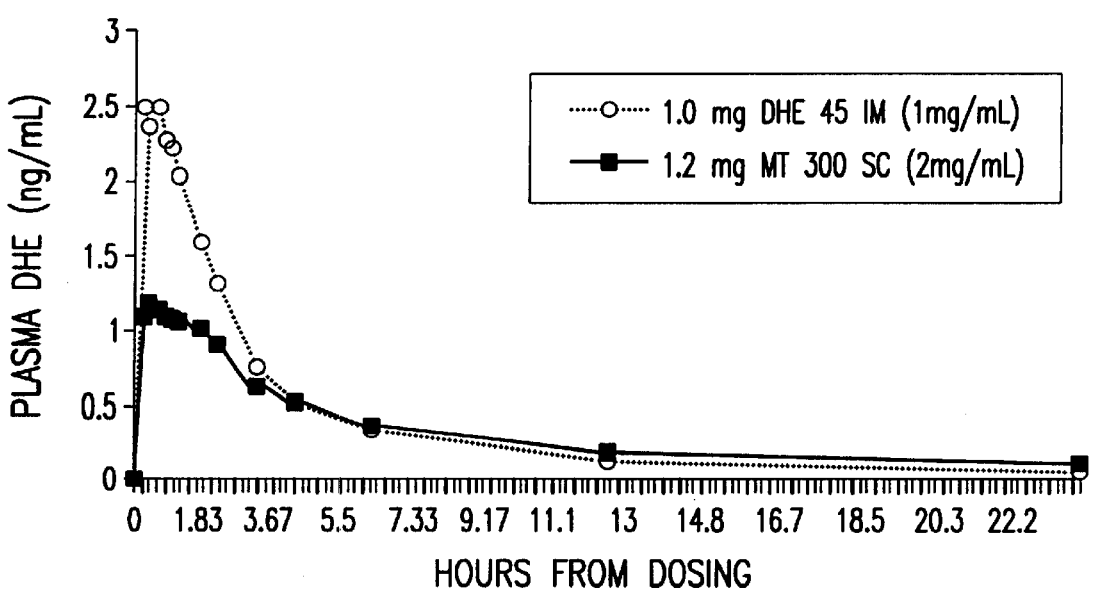
FIG. 3.

The mean plasma DHE concentration-time profile is shown in FIG. 3. These data confirm the lower peak concentration and more prolonged DHE plasma concentration-time profile observed with the 2 mg/ml (2.9 mM) formulations of MT 300 in the initial protocol. The 72-hour blood sampling period in this study permits a comparison of the extent of exposure for the two treatments. The dose corrected mean AUC-infinity is 8.23(±2.04) ng*hr/ml for MT 300 and 9.41(±1.23) ng*hr/mi for DHE 45®, indicating that the systemic DHE exposure is similar following intramuscular DHE 45°(1 mg/ml, 1.5 mM) and subcutaneous MT 300 (2 mg/ml, 2.9 mM). This finding of similarity of bioavailability following intramuscular and subcutaneous administration is consistent with the report by Schran et al. (Curr. Ther. Res. 55:1501–1508 (1994)). No significant levels of the 8-OH DHE metabolite are found after either treatment.

Example 4
Overall Tolerance Profile

Table 4 summarizes the adverse events reported by subjects administered preparations of DHE. Adverse events occur in 20 of 33 subjects treated with MT 300 and 8 of 13 subjects treated with DHE 45®. Analysis of the MT 300 tolerance data according to the number of doses administered reveals that the incidence of nausea is relatively low at 8%. The higher incidence of nausea in the DHE 45® group suggests a difference in the tolerance of the two products.

TABLE 4

Tolerance Profile of Subjects Administered DHE[1]

|  | 1 mg MT 300 (48 exposures) | 1.2 mg MT 300 (7 exposures) | 2 mg MT 300 (8 exposures) | All MT 300 (63 exposures) | 1 mg DHE 45 (13 exposures) |
|---|---|---|---|---|---|
| Nausea | 4 | 1 | 0 | 5 (8%) | 4 (31%) |
| Light-headedness | 1 | 1 | 1 | 3 (5%) | 3 (23%) |
| Leg cramps | 0 | 3 | 0 | 3 (5%) | 2 (15%) |
| Headache | 1 | 0 | 1 | 2 (3%) | 1 (8%) |
| Muscle pain/leg pain | 3 | 0 | 0 | 3 (5%) | 2 (15%) |
| Heart block[2] | 2 | 0 | 0 | 2 (3%) | 0 |
| Cold extremities | 1 | 0 | 0 | 1 (2%) | 1 (8%) |
| Dizziness | 1 | 0 | 0 | 1 (2%) | 0 |
| Chest pain | 1 | 0 | 0 | 1 (2%) | 0 |
| Weakness | 0 | 0 | 1 | 1 (2%) | 0 |
| Feels high | 1 | 0 | 0 | 1 (2%) | 0 |
| Faintness | 1 | 0 | 0 | 1 (2%) | 0 |
| Tired | 0 | 0 | 0 | 0 | 1 (8%) |

TABLE 4-continued

Tolerance Profile of Subjects Administered DHE[1]

|  | 1 mg MT 300 (48 exposures) | 1.2 mg MT 300 (7 exposures) | 2 mg MT 300 (8 exposures) | All MT 300 (63 exposures) | 1 mg DHE 45 (13 exposures) |
|---|---|---|---|---|---|
| Stomach cramps | 1 | 0 | 0 | 1 (2%) | 0 |
| Vomited | 2 | 0 | 1 | 3 (5%) | 0 |

[1]MT 300 preparations are administered subcutaneously and DHE 45 preparations by im injection.
[2]This event occurs in 1 subject after each of two separate doses of MT 300. The subject receives placebo as the second treatment and did not receive DHE 45 ®.

What is claimed is:

1. A therapeutic package comprising:
   (a) a pharmaceutical composition in unit dose form, comprising:
      i) dihydroergotamine (DHE) in an amount such that one or more unit doses of said composition are effective in the symptomatic treatment of migraine headache when administered to a patient; and
      ii) a pharmaceutically acceptable liquid vehicle in which said DHE is dissolved at a concentration of at least 2.9 mM and not more than 7.4 mM; and
   (b) a prefilled syringe or injection ampule containing said pharmaceutical composition.

2. The therapeutic package of claim 1, wherein said pharmaceutical composition is in a prefilled injectable syringe.

3. The therapeutic package of either claim 1 or 2 wherein said pharmaceutical composition further comprises sufficient $CO_2$ or $N_2$ to retard oxidative degradation of said composition.

4. The therapeutic package of claim 2, further comprising an opaque, sealed package from which oxygen has been excluded, said opaque, sealed package containing said prefilled injectable syringe.

5. The therapeutic package of either claim 1 or 2, wherein said pharmaceutical composition further comprises an antioxidant.

6. The therapeutic package of either claim 1 or 2, wherein said DHE is present as dihydroergotamine mesylate.

7. The therapeutic package of either claim 1 or 2, wherein said pharmaceutical composition further comprises caffeine at between a 0.1:1 and 10:1 weight ratio with DHE.

8. The therapeutic package of claim 7 wherein said pharmaceutical composition further comprises sufficient dissolved $CO_2$ or $N_2$ to retard oxidative degradation of said composition.

9. The therapeutic package of claim 7 wherein said pharmaceutical composition further comprises an antioxidant.

10. The therapeutic package of claim 7, wherein said DHE is present as dihydroergotamine mesylate.

11. A therapeutic package made by a process comprising the steps of:
    (a) preparing a unit dose pharmaceutical composition comprising:
       i) dihydroergotamine (DHE) in an amount such that one or more unit doses of said composition are effective in the symptomatic treatment of migraine headache when administered to a patient; and
       ii) a pharmaceutically acceptable liquid vehicle in which said DHE is dissolved at a concentration of at least 2.9 mM and not more than 7.4 mM; and
    (b) prefilling an injectable syringe with said pharmaceutical composition.

12. The therapeutic package of claim 11, wherein said process further comprises enclosing the syringe prefilled with said pharmaceutical composition in an opaque, sealed package from which oxygen has been excluded.

13. The therapeutic package of either claim 11 or 12, wherein said pharmaceutical composition further comprises caffeine at between a 0.1:1 and 10:1 weight ratio with DHE.

14. The therapeutic package of claim 13, wherein said pharmaceutical composition further comprises sufficient $CO_2$ or $N_2$ to retard oxidative degradation of said composition.

15. The therapeutic package of claim 13, wherein said pharmaceutical composition further comprises an antioxidant.

16. The therapeutic package of claim 13, wherein said DHE is present as dihydroergotamine mesylate.

17. In a unit dose pharmaceutical composition containing a solution of DHE and indicated for use in the treatment of migraine headache by injection, the improvement which comprises making the concentration of DHE in said composition at least 2 mg/ml and not more than 5 mg/ml.

18. The improvement of claim 17, further comprising dissolving carbon dioxide or nitrogen in said pharmaceutical composition at a concentration sufficient to retard oxidative degradation of said composition.

* * * * *